US005765560A

United States Patent [19]
Verkerke et al.

[11] Patent Number: 5,765,560
[45] Date of Patent: Jun. 16, 1998

[54] TRACHOSTOMA VALVE AND TISSUE CONNECTOR AND HOUSING FOR USE AS A PART THEREOF

[75] Inventors: Gijsbertus Jacob Verkerke, EP Haren; Gerhard Rakhorst, SN Groningen, both of Netherlands

[73] Assignee: Adeva Medical, Gesellschaft fur Entwicklung und Vertrieb von Medizinischen, Implantat-Artikeln mbH, Germany

[21] Appl. No.: 670,843

[22] Filed: Jun. 28, 1996

Related U.S. Application Data

[63] Continuation of Ser. No. 244,738, filed as PCT/NL92/00227 Dec. 16, 1992, abandoned.

[30] Foreign Application Priority Data

Dec. 16, 1991 [NL] Netherlands ............... 9102095

[51] Int. Cl.$^6$ ................................. A61M 25/00
[52] U.S. Cl. ................. 128/201.16; 128/207.12; 128/911; 128/912; 128/200.26
[58] Field of Search ............... 128/207.16, 207.12, 128/911, 912, 200.26, 201.22, 201.28, 206.15, 203.11, 207.14; 623/9

[56] References Cited

U.S. PATENT DOCUMENTS

| | | | |
|---|---|---|---|
| 3,137,299 | 6/1964 | Tabor | 128/27.16 |
| 3,844,290 | 10/1974 | Birch et al. | 128/207.16 |
| 3,952,335 | 4/1976 | Soree et al. | 128/207.16 |
| 4,325,366 | 4/1982 | Tabor | 128/207.16 |
| 4,538,607 | 9/1985 | Saul | 128/207.16 |
| 4,582,058 | 4/1986 | Debel et al. | 128/207.16 |
| 4,596,248 | 6/1986 | Lieberman | 128/207.16 |
| 4,614,516 | 9/1986 | Bloom et al. | 623/9 |

FOREIGN PATENT DOCUMENTS

| | | | |
|---|---|---|---|
| 0078685 | 10/1982 | European Pat. Off. | A61M 16/00 |
| 2164424 | 3/1986 | United Kingdom | A61M 16/04 |
| PCT/EP86/ 00274 | 5/1986 | WIPO | A61M 16/20 |

*Primary Examiner*—V. Millin
*Assistant Examiner*—V. Srivastava
*Attorney, Agent, or Firm*—Gifford, Krass, Groh, Sprinkle, Patmore, Anderson & Citkowski, P.C.

[57] ABSTRACT

A tracheostoma valve includes a shut-off valve member (1) capable of shutting off the valve in response to an egressive air thrust. The valve includes a blow-off valve member (2) of a design such that the valve can open in response to an overpressure in the trachea which exceeds a given value. This blow-off valve member limits the maximum achievable overpressure behind the valve. Coughing is possible without prior operation of the valve and leakage due to excessive overpressure in the trachea is prevented. The valve may contain a tissue connector and a housing to be connected thereto.

17 Claims, 2 Drawing Sheets

TRACHOSTOMA VALVE AND TISSUE CONNECTOR AND HOUSING FOR USE AS A PART THEREOF

This application is a Continuation of Ser. No. 08/244,738 filed Sep. 7, 1994 now abandoned.

BACKGROUND OF THE INVENTION AND FIELD OF THE INVENTION

The invention relates to a tracheostoma valve with a shut-off valve member capable of shutting off the valve in response to an air displacement.

THE PRIOR ART

In patients with disorders involving the closure or at any rate a reduction of the connection between the trachea and the pharynx, it is known to have the trachea terminate at the throat via a stoma (opening in the skin).

Such a connection of the trachea to the environment is for instance fitted in patients who have been treated for an extensive malignant tumor in the larynx by removing the larynx (including vocal chords and epiglottis) and in whom the trachea has been closed at the former larynx.

In order to maintain at least some possibility of speaking, new vocal chords are formed in the pharynx from muscular tissue, mucous membrane or connective tissue. Further, another valve is fitted in the wall between the trachea and the esophagus, capable of allowing air to pass to the esophagus in the case of overpressure in the trachea. For realizing an overpressure in the trachea, a tracheostoma valve of the type described in the opening paragraph hereof is used. The patient can close this valve by expelling breath relatively quickly. Subsequently, due to overpressure in the trachea, an airstream is realized through the further valve and along the substitute vocal chords for setting those vocal chords into vibration.

A tracheostoma valve as described above is, for instance, commercially available under the designation of "ESKA-Herrmann valve" and is marketed by the firm of ESKA of Lubeck, FRG.

A drawback of such valves is that they also shut off the trachea in the case of fast egressive airstreams due to coughing. In order to avoid this, the valve member should be removed from the valve before coughing or the shut-off valve member should be adjusted to a coughing position.

A further drawback which presents itself in the use of such known valves is the frequent occurrence of leakage between the valve and the stoma, causing interfering noise during speech which, moreover, further impairs the patient's audibility, which is impaired as it is.

SUMMARY OF THE INVENTION

The object of the invention is to render it possible to cough without prior operation of the valve and to overcome the leakage problem described above.

According to the invention, this object is realized by providing a tracheostoma valve of the type described in the opening paragraph hereof with a blow-off valve member which opens in response to a particular overpressure achieved on one side thereof.

The blow-off valve member opens automatically upon coughing, so that operating the valve prior to coughing is unnecessary. Peaks in overpressure that occur during coughing are limited to the height of the overpressure at which the blow-off valve member opens. As a result, the load on the connection of the valve to the stoma is limited, so that leakage is avoided or at any rate prevented.

Because the valve according to the invention does not require any operation by the patient, it can also be applied in situations where the patient, due to a trauma, is suddenly no longer able to breathe via the larynx and through the mouth or nose and a temporary stoma must be made in the trachea, while there is no opportunity to instruct the patient about the use of the valve.

The invention is also embodied by a tissue connector and by a housing for use as a part of a valve according to the invention. The tissue connector can be implanted in the stoma permanently, providing an improved sealing along the edge of the stoma, so that leakage is further prevented. The valve further comprises a housing in which the valve members are mounted. This housing of the valve can be easily placed into the tissue connector by the patient and can also be easily removed therefrom.

The invention will be further illustrated hereinafter with reference to a preferred exemplary embodiment of the invention, in which:

DESCRIPTION OF A PREFERRED EMBODIMENT OF THE INVENTION

Figure 1:
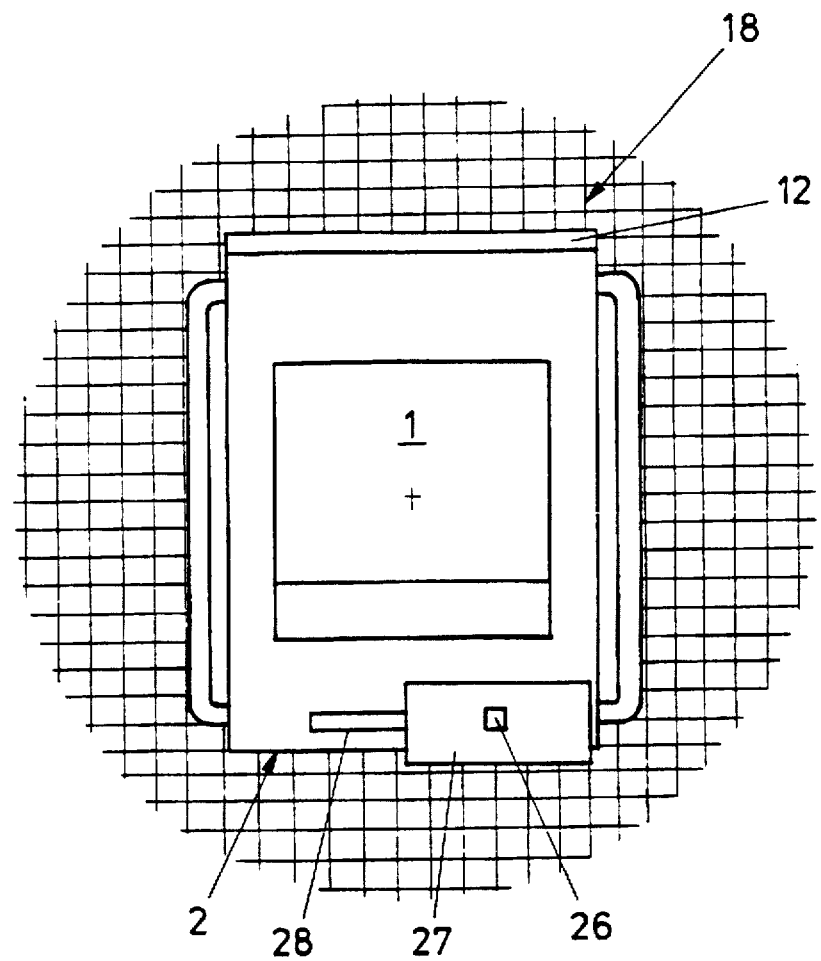
FIG. 1 is a front view of a tracheostoma valve according to the invention.
Figure 2:
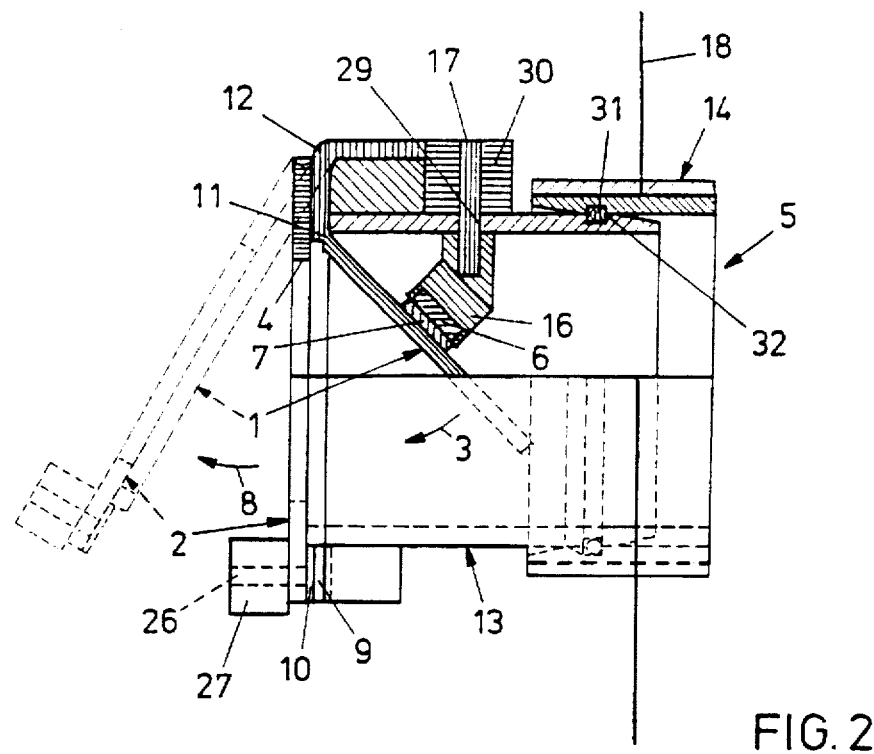
FIG. 2 is a side view, partly in section, of the valve according to FIG. 1.

FIGS. 1 and 2 show a tracheostoma valve according to the invention, capable of being placed, with its end portion 5 on the side of the trachea of a patient, into a stoma communicating with the trachea. The valve comprises a shut-off valve member 1 adapted to shut off the valve in response to a rapid air displacement, brought about by exhaling quickly. In FIG. 2, shut-off valve member 1 is shown in open position by solid lines and in closed position by broken lines. The valve further comprises a blow-off valve member 2, designed so as to open in response to a particular overpressure achieved on the side of end portion 5 of the valve. In FIG. 2, blow-off valve member 2 is shown in closed position by solid lines and in open position by broken lines.

Shut-off valve member 1 is pivotally suspended in the area of its upper edge 11 and is held in the open position by a magnet 6, which exerts a force on a countermagnet plate 7 mounted on valve member 1. When the patient carrying the valve shown expels breath at a particular minimum speed, shut-off valve member 1 will be caught by the airstream and moved in the direction indicated by an arrow 3, and shut off the opening 4 as long as an overpressure is maintained in the valve. Upon inhaling, shut-off valve member 1 is opened again and held in the open position by magnet 6.

Blow-off valve member 2 is likewise pivotally suspended in the area of its upper edge 12, but is held in its closed position by a magnet 9, exerting a force on a countermagnet plate 10 mounted on valve member 2. When the overpressure on the side 5 of valve member 2 exceeds a particular value, this valve member 2 is pushed open, pivoting in the direction indicated by an arrow 8. Blow-off valve member 2 preferably opens at an overpressure just exceeding the overpressure which occurs during speech, so that the air duct is also cleared in cases of a lighter cough and the maximum overpressure behind the valve is kept as small as possible. Further, by limiting the maximum overpressure in the air duct, leakage is prevented.

In the valve according to the exemplary embodiment shown, opening 4, closable by shut-off valve member 1, is provided in blow-off valve member 2. This offers the advantage that when blow-off valve member 2 is opened, shut-off valve member 1 has pivoted with it, so that already at a relatively small cross-sectional area of the valve as a whole, a passage area is provided which is sufficiently large for the passage of air. This applies to the passage of the blow-off valve member as well as to the passage of the shut-off valve member. As a result, the valve as a whole can be made of a particularly compact design. Further, a small cross-sectional area of the valve is advantageous for limiting the force exerted on the valve by an overpressure in the trachea.

Utilizing a magnet 9 for holding blow-off valve member 2 in the closed position has the advantage that it is released for a long time at an accurate, constant force, and that the means for retaining blow-off valve member 2 are of a simple construction and easy to clean. A particular advantage of utilizing a magnet 9 for holding blow-off valve member 2 in the closed position is that this magnet, upon closure of the valve member, does not offer any resistance and, moreover, shuts blow-off valve member 2 independently.

Of course, other means for holding and, at a particular overpressure, releasing the blow-off valve member can be used as well, such as an elastic resistance or a spring system with a strongly decreasing closing force at an increasing opening angle. As regards the shut-off valve member, too, instead of a magnetic stop mechanism—here in the open position—other means can be used for holding open that valve member.

In the device according to the exemplary embodiment shown, a first part 10 of the magnet closure is slidable relative to a second part 9 of the magnet closure, in a direction transverse to the opening direction 8 of blow-off valve member 2, for adjusting the effective overlap of the magnet closure. Thus, a simple and effective construction is obtained for a stepless adjustment of the overpressure at which blow-off valve member 2 opens. Countermagnet plate 10 is slidable relative to magnet 9. To that end, countermagnet plate 10 is connected to a slide 27 via a bar 26. The bar is slidable in a slot 28. When blow-off valve member 2 is closed, slot 28 is located outside the passage of the valve, so that no leakage through slot 28 can occur.

Magnet 6 for holding shut-off valve member 1 is also slidable in a similar manner. Magnet 6 is mounted in a magnet holder 16. Magnet holder 16 is connected to-an adjusting slide 30 via a bar 17 extending through a slot 29, so that slide 30 and magnet holder 16 are slidable, guided by the slot. By sliding adjusting slide 17, the overlap between magnet 6 and countermagnet plate 7 is adjusted. The smaller the overlap, the weaker the air thrust that is required for closing shutoff valve member 1.

Shut-off valve member 1 is preferably made from soft, flexible and vibration-damping material, so as to limit noise, like ticking, during closure of shut-off valve member 1.

The valve according to the preferred exemplary embodiment shown has a substantially rectangular cross-section. This has the advantage that in a stoma which forms an opening in a given number of successive cartilage rings 33 (FIG. 3) of the air tube, the valve has a passage of a maximum cross-sectional area, so that a relatively small valve is sufficient to provide a sufficiently large passage area. Moreover, a better connection of the tracheostoma valve to adjacent non-interrupted cartilage rings 33 of the trachea is obtained. Cartilage rings 33 are formed by horseshoe-shaped elements of cartilage, which have their open end facing dorsally and each extend around the trachea. Cartilage rings 33 are disposed behind each other in longitudinal direction of the trachea.

Known valves are removed for the night's rest, so that the tissue around the stoma can contract again at night and connects closely to the valve again during the daytime. In cases where the re-contraction of this tissue does not compensate the withdrawal thereof, the attachment of the tissue to the valve along the edge of the stoma will worsen increasingly in the course of time, which eventually will lead to leakage along the valve during speech.

This problem is avoided in the valve according to the exemplary embodiment shown, in that this valve comprises a housing 13 and a tissue connector 14, with the housing 13 being detachably mounted in the tissue connector 14. The housing can be removed, for instance for cleaning or prior to the night's rest, while the tissue connector can remain in the stoma and can therefore be constructed as an implant.

Figure 3:
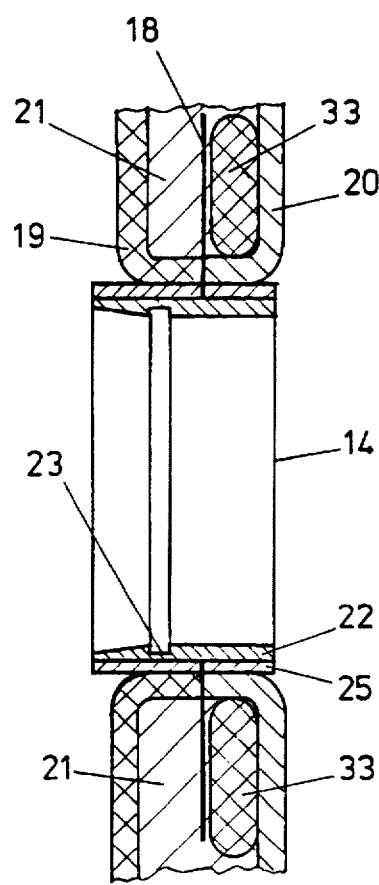
FIG. 3 is a sectional view of a tissue connector for use in a tracheostoma valve according to the invention.

FIG. 3 shows tissue connector 14 in implanted condition. This drawing further shows a connecting edge 23, which can be engaged by an O-ring, provided around housing 13 (FIG. 2) of the valve. The O-ring 31 is disposed in a circular groove 32 in housing 13.

To obtain a stable, reliable implantation of tissue connector 14, this connector is provided with a thin-walled flange 18 of biocompatible material, extending in radial direction around the valve. In implanted condition (FIG. 3), flange 18 is anchored in connective tissue 21 of the throat and preferably extends from an inner ring 22 which is provided with a synthetic layer 25. The synthetic layer preferably comprises a coating of biocompatible material. Thus, a stable anchoring of flange 18 in tissue connector 14 is obtained.

Flange 18 is preferably made of coarse-mesh polypropylene gauze, capable of being held firmly by connective tissue 21. As shown schematically in FIG. 3, connected to the flange on one side thereof is mucous membrane 20 of the trachea, and on the other side skin 19 of the throat. It is observed that such a tissue connector can also be used in stoma's elsewhere, such as an intestinal stoma. In that case, instead of a housing of a valve, a connecting means of a suitable recipient is connected to the tissue connector.

We claim:

1. A tracheostoma valve with a shut-off valve member capable of shutting off the tracheostoma valve in response to an air displacement, and a blow-off valve member which opens in response to a particular overpressure achieved, and a magnet closure for holding the shut-off valve member (1) in the closed position, with a first part (6) of the magnet closure being slidable relative to a second part (7) of said magnet closure, in a direction transverse to the opening direction of the shut-off valve member (1), for adjusting the over pressure position.

2. A valve according to claim 1 and said blow-off valve member (2) comprises an opening (4) which is closable by the shut-off valve member (1).

3. A valve according to claim 1, further comprising a first part (9) of said magnet closure being slidable relative to a second part (10) of said magnet closure in a direction transverse to the opening direction of blow-off valve member (2), for adjusting the effective overlap of the magnet closure.

4. A valve according to claim 1, further comprising said valve having a passage with a substantially rectangular cross-section.

5. A valve according to claim 1, further comprising a housing (13) and a tissue connector (14), with the housing (13) being detachably mounted in the tissue connector (14).

6. A valve according to claim 5, characterized in that the tissue connector (14) comprises a thin-walled flange (18) of biocompatible material, extending in radial direction around the valve.

7. A valve according to claim 6, characterized in that the flange (18) is made of coarse-mesh polypropylene gauze.

8. A tissue connector for use as a part of a valve according to claim 5.

9. A housing for use as a part of a valve according to claim 5.

10. A tracheostoma valve with a shut-off valve member capable of shutting off the tracheostoma valve in response to an air displacement, and a blow-off valve member which opens in response to a particular overpressure achieved on one side thereof; and a magnet closure for holding the shut-off valve member (1) in the closed position, with a first part (6) of the magnet closure being slidable relative to a second part (7) of said magnet closure, in a direction transverse to the opening direction of the shut-off valve member (1), for adjusting the overpressure by varying an overlap of the magnet closure.

11. A valve according to claim 10, characterized by a magnet closure for holding the blow-off valve member (2) in the closed position.

12. A valve according to claim 10, further comprising said valve having a passage with a substantially rectangular cross-section.

13. A valve according to claim 10, further comprising a housing (13) and a tissue connector (14), with the housing (13) being detachably mounted in the tissue connector (14).

14. A valve according to claim 13, characterized in that the tissue connector (14) comprises a thin-walled flange (18) of biocompatible material, extending in radial direction around the valve.

15. A valve according to claim 14, characterized in that the flange (18) is made of coarse-mesh polypropylene gauze.

16. A tissue connector for use as a part of a valve according to claim 13.

17. A housing for use as a part of a valve according to claim 13.

* * * * *

UNITED STATES PATENT AND TRADEMARK OFFICE
CERTIFICATE OF CORRECTION

PATENT NO. : 5,765,560
DATED : June 16, 1998
INVENTOR(S) : Gijsbertus Jacob Verkerke Gerhard Rakhorst It is certified that error appears in the above-identified patent and that said Letters Patent is hereby corrected as shown below:

Column 2, line 39, delete " - " between --valve comprises--.
Column 3, line 52, delete " - " after --connected to--.

Signed and Sealed this

Fifth Day of January, 1999

Attest:

Attesting Officer

Acting Commissioner of Patents and Trademarks